United States Patent [19]

Weber et al.

[11] 4,170,518
[45] Oct. 9, 1979

[54] MICROBIOLOGICAL CONVERSION OF STEROL DERIVATIVES TO 5-ANDROSTEN-17-ONE DERIVATIVES AND THEIR USE

[75] Inventors: Alfred Weber; Mario Kennecke; Alfred Popper; Rudolf Müller; Ulrich Eder; Gregor Haffer; Gerhard Sauer; Günter Neef; Rudolf Wiechert, all of Berlin, Fed. Rep. of Germany

[73] Assignee: Schering Aktiengesellschaft, Bergkamen and Berlin, Fed. Rep. of Germany

[21] Appl. No.: 710,559

[22] Filed: Jul. 30, 1976

[30] Foreign Application Priority Data

Aug. 1, 1975 [DE] Fed. Rep. of Germany ....... 2534911

[51] Int. Cl.² .............................................. C07B 29/02
[52] U.S. Cl. ...................................................... 435/55
[58] Field of Search ........................................ 195/51 G

[56] References Cited

U.S. PATENT DOCUMENTS 3,759,791  9/1973  Marsheck et al. ................. 195/51 G

OTHER PUBLICATIONS

Buki et al, Acta Microbiol. Acad. Sci. Hung. 22, 447–451, (1975).

Primary Examiner—Alvin E. Tanenholtz
Attorney, Agent, or Firm—Millen & White

[57] ABSTRACT

Sterol derivatives of the formula

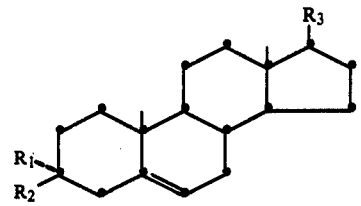

wherein $R_1$ is a hydrogen atom and $R_2$ is lower alkoxy, or $R_1$ and $R_2$ collectively are lower alkylenedioxy and $R_3$ is a sterol hydrocarbon side chain are converted to the corresponding androsten-17-ones by the oxidative degradation activity of a species of microorganism which degrades sterol side chains, preferably of the genus Mycobacterium. The ether group of those compounds wherein $R_1$ is a hydrogen atom and $R_2$ is lower alkoxy, and the corresponding 17β-hydroxy and 17α-hydrocarbon-17β-hydroxy compounds is cleaved by reaction with an alkanoic acid chloride or anhydride in the presence of a Lewis acid.

10 Claims, No Drawings

MICROBIOLOGICAL CONVERSION OF STEROL DERIVATIVES TO 5-ANDROSTEN-17-ONE DERIVATIVES AND THEIR USE

BACKGROUND OF THE INVENTION

This invention relates to processes for the microbiological conversion of sterol derivatives to 5-androsten-17-one derivatives and their use.

It is known in the prior art that numerous microorganisms, such as, for example, those of the genera Arthrobacter, Brevibacterium, Microbacterium, Protaminobacter, Bacillus, Norcardia, Streptomyces, and especially Mycobacterium, have the natural ability to degrade zoosterols and phytosterols to carbon dioxide and water, with 4-androstene-3,17-dione and 1,4-androstadiene-3,17-dione are formed as intermediates.

Since numerous zoosterols and phytosterols, e.g., cholesterol, stigmasterol, capesterol, brassicasterol, and the sitosterols, are widely found in nature and thus are readily accessible raw materials for the synthesis of pharmacologically effective steroids, numerous investigations have been conducted to control the degradation of the sterols during fermentation so that further degradation of the thus-formed 4-androstene-3,17-dione and 1,4-androstadiene-3,17-dione is prevented.

For example, it is possible to prevent the further degradation of 1,4-androstadiene-3,17-dione and 4-androstene-3,17-dione by adding inhibitors to the fermentation batches. See Federal Republic of Germany Unexamined Laid-Open Applications DOS's Nos. 1,543,269 and 1,593,327 and U.S. Pat. No. 1,208,078. However, the use of such inhibitors makes these reactions very expensive on a commercial scale because, inter alia, the inhibitors employed must be removed from the fermentation cultures after the reaction has been accomplished to avoid discharging them into the waste water. Moreover, these conventional reactions have the disadvantage that they always produce 1,4-androstadiene-3,17-dione, alone or as a mixture with 4-androstene-3,17-dione and 1,4-androstadiene-3,17-dione is a poor starting material for the synthesis of numerous pharmacologically active steroids.

The further degradation of 1,4-androstadiene-3,17-dione and of 4-androstene-3,17-dione can also be prevented by using mutated microorganisms of the genus Mycobacterium for the fermentative conversion of the sterols. See U.S. Pat. No. 3,684,657. These mutants, however, have the disadvantage that they have a very limited capability for producing 1,4-androstadiene-3,17-dione or 4-androstene-3,17-dione from sterols.

It is an object of this invention to provide a process for the side chain degradation of sterols which does not have the disadvantages of known methods. Another object is the provision of a process for the cleavage of the 3-ethers. Other objects will be apparent to those skilled in the art.

SUMMARY OF THE INVENTION

In a process aspect, this invention relates to a process for the production of 4-androsten-17-one derivatives of Formula I

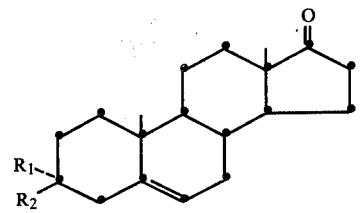

wherein $R_1$ is a hydrogen atom and $R_2$ is lower alkoxy, or $R_1$ and $R_2$ collectively are lower alkylenedioxy, which comprises subjecting a sterol derivative of Formula II

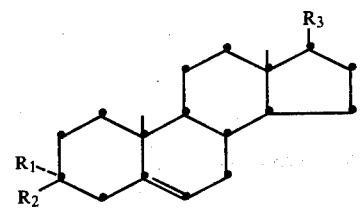

wherein $R_1$ and $R_2$ have the values given above and $R_3$ is a sterol hydrocarbon side chain of 8–10 carbon atoms, to the oxidative degradation activity of a culture of a microorganism which degrades sterol side chains to 17-keto groups.

In another process aspect, this invention relates to a process for the cleavage of the 3-ether group of a thus-produced 5-androsten-17-one wherein $R_1$ is H and $R_2$ is lower-alkoxy, or of a corresponding 17β-hydroxy compound, or of a corresponding 17α-hydrocarbon-17β-hydroxy compound, by reaction with an alkanoic acid chloride or anhydride in the presence of a Lewis acid, to produce a compound of general Formula III

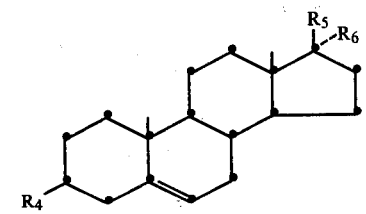

wherein $R_4$ is alkanoyloxy as defined above and $R_5$ and $R_6$ collectively are an oxygen atom or $R_5$ is alkanoyloxy and $R_6$ is a hydrogen atom or lower saturated or unsaturated hydrocarbon.

DETAILED DISCUSSION

It is surprising that by the fermentative conversion of this invention, 5-androsten-17-one derivatives of general Formula I are produced in high yields, because it is known that the side chain degradation of sterols is achieved by a very complex fermentation system and it could not be predicted that all of the enzymes cooperating in the side chain degradation of natural steroids also possess the capacity of effecting the selective side chain degradation of the sterol derivatives of general Formula II which do not occur in nature. Moreover, it could not be predicted that the enzyme systems capable of degrading of 1,4-androstadiene-3,17-dione and of 4-androstene-3,17-dione are incapable of degrading the 5-androsten-17-one derivatives of general Formula I.

In the above formulae, when $R_2$ is lower alkoxy, it preferably is alkoxy of 1–4 carbon atoms, e.g., propoxy and butoxy, more preferably methoxy and ethoxy.

When $R_1$ and $R_2$ collectively are alkylenedioxy, alkylenedioxy preferably is of 2–6 carbon atoms, and 2–3 carbon atoms bridging the oxygen atoms, e.g., 1,2-ethylenedioxy, 1,2-propylenedioxy, 1,3-propylenedioxy, 2-methyl-1,3-propylenedioxy, 2,2-dimethyl-1,3-propylenedioxy, 2,3-butylenedioxy and 1,3-butylenedioxy.

Examples of $R_3$ hydrocarbon groups of 8–10 carbon atoms are the saturated and unsaturated side chains of naturally occurring zoosterols and phytosterols, e.g., the side chain of cholesterol, stigmasterol, campesterol, brassicasterol, and the sitosterols.

Examples of starting sterol derivatives of general Formula II are compounds of general Formula IIa

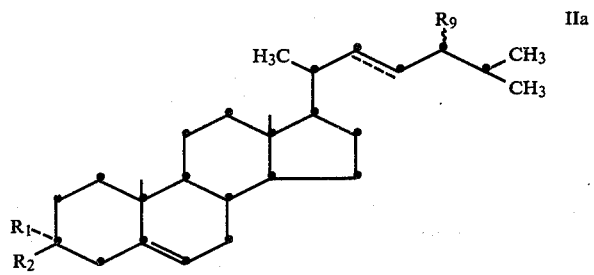

wherein $R_1$ and $R_2$ have the values given above, the bond $\equiv\equiv\equiv$ is a single or double bond and $R_9$ is a hydrogen atom, methyl or ethyl.

Apart from the use of starting compounds of Formula II and conducting the fermentation in the absence of inhibitors, the process of this invention is accomplished under the same fermentation conditions which are also utilized in the conventional microbiological side chain degradation reactions of sterols, e.g., the Federal Republic of Germany applications and the U.S. Patent cited above, whose disclosures are incorporated by reference.

According to this invention, the fermentation is conducted with a culture of a microorganism customarily employed for the side chain degradation of sterols. Suitable cultures are, for example, bacterial cultures capable of the side chain degradation of sterols of the genera Arthrobacter, Brevibacterium, Microbacterium, Protaminobacter, Streptomyces, and preferably of the genus Mycobcterium. Examples of suitable specific microorganisms are: *Microbacterium lactum* IAM-1640; *Protaminobacter alboflavus* IAM-1040; *Bacillus roseus* IAM-1257; *Bacillus sphaericus* ATCC-7055; *Norcardia gardneri* IAM-105; *Morcardia minima* IAM-374; *Norcardia corallina* IFO-3338; *Streptomyces rubescens* IAM-74; or especially the microorganisms *Mycobacterium avium* IFO-3082, *Mycobacterium phlei* IFO-3158, *Mycobacterium phlei* (Institute of Health, Budapest No. 29), *Mycobacterium phlei* ATCC-354, *Mycobacterium smegmatis* IFO-3084, *Mycobacterium smegmatis* ATCC-20, *Mycobacterium smegmatis* (Institute of Health, Budapest No. 27), *Mycobacterium smegmatis* ATCC-19979, *Mycobacterium fortuitum* CBS-49566, Mycobacterium spec. NRRL-B-3805, and Mycobacterium spec. NRRL-B-3683.

The cultivation of the microorganism is ordinarily conducted in a suitable nutrient medium with aeration by employing submerged fermentation culturing conditions conventionally employed for these microorganisms. Thereafter, the substrate, i.e., a compound of Formula II, (dissolved in a suitable solvent or preferably in the form of an aqueous emulsion) is added to the culture and fermentation is continued until maximum substrate conversion has been achieved.

Suitable substrate solvents are, for example, methanol, ethanol, glycol monomethyl ether, dimethylformamide, and dimethyl sulfoxide. The substrate can be emulsified, for example, by introducing the latter through nozzles in a micronized form or dissolved in a water-miscible solvent (such as methanol, ethanol, acetone, glycol monomethyl ether, dimethylformamide, or dimethyl sulfoxide) under strong turbulence into (preferably decalcified) water containing a conventional emulsifier, e.g., nonionic emulsifiers, such as, for example, ehtylene oxide adducts or fatty acid esters of polyglycol. Specific examples of suitable emulsifiers are the conventional commercial surfactants, such as "Tegin", "Tagat", "Tween", and "Span."

Especially in the case of the 3-alkoxy compounds of general Formula II, the emulsification of the substrates makes it possible to achieve an increased throughput of substrate and thus an increase in substrate concentration. However, it is also possible, of course, to utilize in the process of this invention other methods for increasing substrate throughput, which are well known to those skilled in the fermentation art.

The optimum substrate concentration, instnt of adding the substrate, and duration of fermentation are dependent on the structure of the substrate employed and the species of microorganism utilized. These variables can be determined in an individual case by preliminary experiments familiar to those skilled in the art and generally required in microbiolobical steroid conversions.

The conversion of 5-androsten-17-one derivatives of general Formula I wherein $R_1$ and $R_2$ are lower alkylenedioxy to obtain pharmacologically active steroids does not present any difficulties. Thus, the ketal group of these compounds can be split off, for example, optionally after reducing the 17-keto group with sodium borohydride, hydrolytically with the aid of acids, thus forming the known steroids 4-androstene-3,17-dione and testosterone.

In contrast thereto, the ether group of the 5-androsten-17-one derivatives of general Formula I wherein $R_1$ is a hydrogen atom and $R_2$ is lower alkoxy can be cleaved only with relatively great difficulty. Although numerous methods are known for the splitting of ether bonds, most of the conventional ether splitting methods are unsuitable to cleave the ether group of these compounds.

Accordingly, on another process aspect, this invention relates to a process for the cleavage of the ether group of 3-alkoxy compounds of general Formula I and corresponding 17-hydroxy compounds, in a simple manner and in high yields.

According to this process, a compound of general Formula Ia

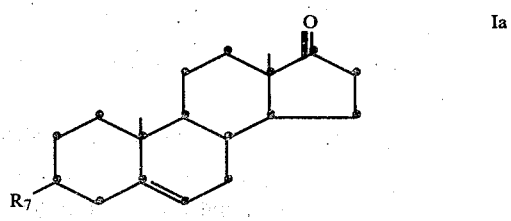

wherein R₇ is lower alkoxy, or a corresponding 17β-hydroxy-compound, or a corresponding 17α-hydrocarbon, 17β-hydroxy-compound, i.e., compounds of the formula

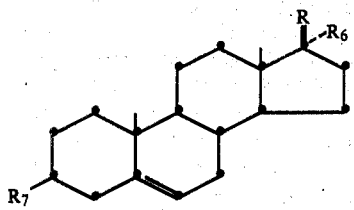

wherein R₇ is lower akoxy and R and R₆ collectively are an oxygen atom or R is OH and R₆ is H or saturated or unsaturated hydrocarbon group, in the presence of a Lewis acid with an acid chloride or anhydride of an alkanecarboxylic acid, i.e., of an acid of the formula R₄H wherein R₄ is alkanoyloxy.

The compounds of Formula Ib wherein R is Oh and R₆ is H are produced by reducing the corresponding compounds of Formula Ia in a conventional manner, e.g., with sodium borohydride or lithium aluminum hydride, and those wherein R is OH and R₆ is hydrocarbon are produced by reacting the corresponding compounds of Formula Ia wth an organometallic compound of general Formula IV MeR₈                                                  IV wherein R₈ is a lower saturated or unsaturated hydrocarbon group and Me is an alkali metal atom or a magnesium halide group.

Preferred R₄ alkanoyloxy groups are those of 2–12 carbon atoms, more preferably 2–8 carbon atoms, e.g., acetoxy, propionyloxy, butyryloxy, pentanoyloxy, hexanoyloxy, heptanoyloxy and octanoyloxy.

Examples of preferred R₆ lower saturated or unsaturated hydrocarbon groups are those of 1–4 carbon atoms, preferably methyl, ethyl, vinyl, and ethynyl.

The thus-prepared 5-androstene derivatives of general Formula III are pharmacologically active steroids or valuable intermediates for the production of pharmacologically active steroids.

For example, esters of 3β-hydroxy-5-androsten-17-one espcially lower akonoic esters, are distinguished by androgenic activity (Chem. Abstr. 65, 1966, 12264 f); and the higher esters of this compound are useful for the treatment of climacteric complaints in combination with estrogens. Federal Republic of Germany Unexamined Laid-Open Application No. 1,643,046.

The compounds of general Formula III wherein R₅ is alkanoyloxy yield, after saponification and subsequent Oppenauer reaction (for example, by heating the saponification products in bezene-acetone with aluminum isopropylate), the corresponding derivatives by conventional ether splitting methods. However, as stated above, the thus-obtained yields are normally very unsatisfactory.

By the process of this invention, the 3-alkoxy-5-androstene derivatives (Formula Ib) can be reacted, in the presence of Lewis acids, with an acid chloride or preferably an anhydride of an alkanecarboxylic acid (an ether splitting method which is known per se), to produce the 5-androstene derivatives of general Formula III, which are obtained in high yields. Acetic anhydride is preferred. Lewis acids are employed as catalysts. Those which do not enter into nucleophilic substitution reactions are preferred. Suitable Lewis acids are, for example, aluminum fluoride, magnesium perchlorate, and especially boron trifluoride etherate.

This reaction can be conducted utilizing the acid chloride or preferably the acid anhydride also as the solvent. However, it is also possible to conduct the reaction in the presence of an inert solvent, such as chlorinated hydrocarbons (chloroform, dichloromethane, tetrachloroethane, and similar compounds), ethers (dioxane, tetrahydrofuran, glycol dimethyl ether, and similar compounds) and dipolar aprotic solvents (dimethylformamide, hexamethylphosphoric triamide, and similar compounds.) The reaction is preferably conducted at a reaction temperature of 0° C. to 120° C.

It will be apparent to those skilled in the art that it is not always necessary for the ether splitting step to immediately follow the fermentation step. On the contrary, it 17β-hydroxy-3-keto- Δ⁴-steroids which, as is known, likewise have a pronounced hormonal activity, such as, for example, the testosterone, 17α-methyltestosterone, 17α-ethyltestosterone and 17α-ethynyltestosterone.

17α-Ethynyl-17-62 -hydroxy-4-androsten- 3-one and 17β-hydroxy-17α-vinyl-4-androsten-3-one are, as is known, valuable intermediates for the preparation of pharmacologically effective 17α-hydroxyprogesterone and the esters thereof (Helv. Chim. Acta 24, 1941, 945 and DOS 2,140,291).

The reaction of the 17-keto group of the 5-androsten-17-one derivatives of general Formula I is effected by methods well known to those skilled in the art. (See, for example, John Fried: Organic Reactions in Steroid Chemistry, van Nostrand Reinhold Co., New York etc. (1972) 1 : 61 et seq.) Thus, these compounds can be reacted, for example, with sodium borohydride or lithium aluminum hydride, thus obtaining the corresponding 17β-hydroxy-5-androstene derivatives.

Conventional methods can also be employed for alkylating the 17-keto group. (See, for example, John Fried: Organic Reactions in Steroid Chemistry, van Nostrand Reinhold Co., New York etc. (1972) 2 : 53 et seq.) Thus, the 5-androsten-17-one derivatives of general Formula Ia can be reacted, for example, with alkyl magnesium halides or alkali metal acetylides, yielding the corresponding 17β-hydroxy-17α-alkyl-(or-17α-ethynyl)-5-androstene derivatives.

The thus-obtained 3-alkoxy-5-androstene derivatives can be converted into the corresponding 3-hydroxy-5-androstene can often be more advantageous to conduct this reaction step at a later point in time.

Thus, 5-pregnen-20-one derivatives can be prepared, for example, in a simple manner by the steps of:

(a) converting a 5-androsten-17-one derivative of general Formula Ia by reaction with alkali metal acetylide into a 17α-ethynyl compound of general Formula VI

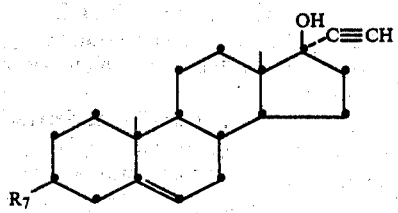

wherein R₇ has the values given above;

(b) dehydrating the latter to a 5,16-pregnadiene derivative of general Formula VII

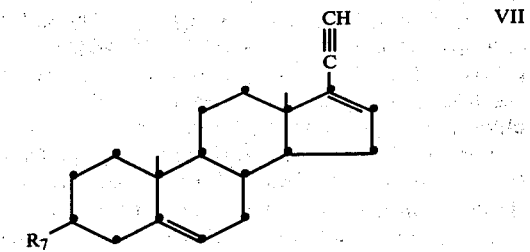

wherein $R_7$ has the values given above;

(c) chemically adding water to the thus-produced 6,17-pregnadiene compound with the aid of a mercury(II) salt to produce a 5-pregnen-20-one derivative of general Formula VIII

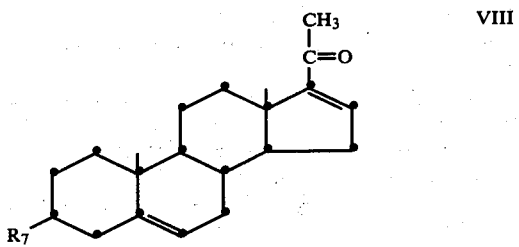

wherein $R_7$ has the values given above;

(d) hydrogenating or methylating with methylmagnesium halide the thus-obtained 5-pregnene-20-derivative; and (e) cleaving the 3-ether group thereof, by reaction in the presence of Lewis acids with an acid chloride or anhydride of an alkanecarboyxlic acid, to produce a 5-pregnene derivative of general Formula V

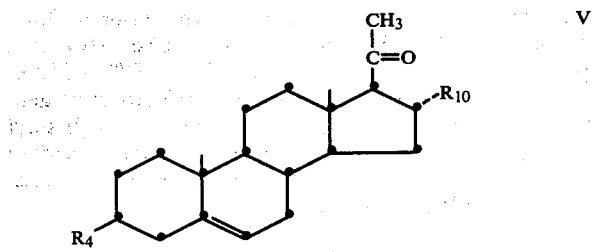

wherein $R_4$ is alkanoyloxy and $R_{10}$ is a hydrogen atom or methyl group.

The 5-pregnene derivatives of general Formula V are valuable intermediates for the synthesis of pharmacologically active steroids. Thus, the compounds of general Formula V wherein $R_{10}$ is a hydrogen atom can be saponified and the product of the saponification can be oxidized by the Oppenauer method to produce progesterone. The compounds wherein $R_{10}$ is a methyl groups are, as in known, valuable intermediates for example, for the preparation of 6α-fluoro-11β,21-dihydroxy-16α-methyl-1,4-pregnadiene-3,20-dione, which has anti-inflammatory activity.

The reacton of the 5-androsten-17-one derivatives of general Formula Ia with alkali metal acetylides has been described. The 17α-ethynyl compounds of general Formula VI formed during this reaction can be conventionally dehydrated. A suitable dehydration method is, for example, the reaction of the acetylenic compounds with a halogenating reagent, e.g., thionyl chloride, phosphorus oxychloride, or methanesulfonic acid chloride, in the presence of pyridine or a pyridine derivative, e.g., lutidine or collidine, optionally in the presence of an inert slent, e.g., benzene, toluene and xylene, at a reaction temperature of 80–160° C. The thus-obtained 5,16-pregnadiene derivatives of general Formula VII can be hydrated in a conventional manner under the conditions customarily employed for the hydration of acetylene compounds. A suitable hydrating method is, for example, the reaction of these compounds in the presence of a mercury(II) salt and water as well as H+ions and in an inert solvent, e.g., an acohol (methanol, ethanol, isopropanol, and similar compounds), a polar ether, e.g., (dioxane, tetrahydrofuran, glycol dimethyl ether, glycol monomethyl ether and similar compounds).

The optional hydrogenation can be conducted according to conventional methods. A suitable hydrogenation method is, for example, the hydrogenation with hydrogen in the presence of Raney nickel, a platinum catalyst, or palladium catalyst.

The optional reaction of the 5,16-pregnadien-20-one drivatives with methylmagnesium halide is also carried out according to known operating methods (John Fried: Organic Reactions in Steroid Chemistry, van Nostrand Reinhold Co., New York etc., [1972], 2:75).

The subsequent ether splitting step is conducted under the conditions described hereinabove.

The 3-alkoxy compounds of general Formula II employed as starting compounds can be prepared by etherifying the corresponding 3-hydroxy compounds, for example, according to the method of J. P. Duszo et al. (Steroids 1966:495–509) by reaction with a trialkyl orthoformic acid ester in the presence of perchloric acid.

The 3-ketals of general Formula II employed as starting compounds can be prepared by oxidizing the corresponding 3-hydroxy compounds, for example, according to the Oppenauer method and then ketalizing the thus-formed 3-keto- $\Delta^4$-steroids by reaction with an alkanediol in the presence of p-toluenesulfonic acid. (C. Djerassi: Steroid Reactions, Holden Day Inc., San Francisco [1963 ]: 3–8 and 92–101.)

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

(A) EXAMPLES OF MICROBIOLOGICAL SIDE CHAIN DEGRADATION

EXAMPLE 1

(a) A 2-liter Erlenmeyer flask is charged with 500 ml. of a sterile nutrient solution containing 1% yeast extract, 0.45% disodium hydrogen phosphate, 0.34% potassium dihydrogen phosphate, and 0.2% "Tween" 80, adjusted to pH 6.7, then inoculated with a dry culture of Mycobacterium spec. NRRL-B-3805, and shaken for 3 days at 190 r.p.m. at 30° C.

(b) 50 g. of cholesterol is suspended in 120 ml. of dichloromethane and 50 ml. of triethyl orthoformate under argon, combined with 0.5 ml. of 70% strength perchloric acid, and agitated for 4 hours at room temperature. The mixture is then poured into water, agitated for two hours, extracted with dichloromethane, the dichoromethane phase is washed, concentrated under vacuum, the residue crystallized from methanol, and the yield is 43.25 g. of 3 β-ethoxy-5-cholestene, m.p. 82°–83° C. 25.0 g. of the thus-prepared 3-ethoxy-5-cholestene is emulsified for 5 minutes with 10 g. of "Tegin" and 750 ml. of water (adjusted to pH 11.3 with sodium hydroxide solution) at 95° C. with an "Ultra-Turrax" mixer (company: Jahnke and Kunkel, Federal Republic of Germany). The emulsion is sterilized for 20 minutes at 120° C.

(c) A 500 ml. Erlenmeyer flask containing 85 ml. of sterile nutrient solution with 2.0% corn steep liquor, 0.3% diammonium hydrogen phosphate, and 0.25% "Tween" 80, adjusted to pH 7.0, is inoculated with 5 ml. of the Mycobacterium spec. subculture, then combined with 14 ml. of the 3β-ethoxy-5-cholestene suspension (corresponding to 0.5 g. of 3-ethoxy-5-cholestene), and shaken for 120 hours at 30° C. and 220 r.p.m.

The fermentation culture is thereafter extracted with tetrachloroethane, the organic phase is concentrated after having been washed, the residue is purified by chromatography over a silica gel column, and the product, in addition to 0.025 g. of 3-ethoxy-5-cholestene and after recrystallization from ethyl acetate, is 0.25 g. of 3β-ethoxy-5-androsten-17-one, m.p. 146°–147° C.

EXAMPLE 2

(a) 50 g. of a stigmasterol raw material is converted into its 3β-ethyl ether under the conditions described in Example 1(b).

25. g. of the thus-obtained crude 3β-ethoxystigmasterol product (purity 92%) is emulsified as set forth in Example 1(b).

(b) 14 ml. of the thus-produced 3β-ethoxystigmasterol suspension (corresponding to 0.46 g. of 3-ethoxystigmasterol) is fermented under the conditions set out in Example 1(c) for 120 hours with a Mycobacterium spec. NRRL-B-3805 culture. After the reaction mixture has been worked up as disclosed in Example 1(c), 0.1 g. of 3β-ethoxystigmasterol and 0.18 g. of 3β-ethoxy-5-androsten-17-one, melting point 146°–147° C., are produced.

EXAMPLE 3

(a) 25 g. of 4-cholesten-3-one is combined with 150 ml. of benzene, 30 g. of glycol, and 0.5 g. of p-toluenesulfonic acid and heated for 24 hours with the use of a water trap.

The mixture is then allowed to cool, diluted with benzene, the benzene phase washed with sodium bicarbonate and water, dried over sodium sulfate, and concentrated under vacuum. The residue is recrystallized from acetone-hexane, thus obtaining 19.6 g. of 3,3-ethylenedioxy-5-cholestene, m.p. 130°–132° C.

Five grams of 3,3-ethylenedioxy-5-cholestene is dissolved at 60° C. in 100 ml. of dimethylformamide.

(b) Under the conditions of Example 1(c), 100 ml. of a Mycobacterium spec. NRRL-B-3805 culture is prepared, combined with 1 ml. of 3,3-ethylenedioxy-5-cholestene solution, and fermented for 96 hours.

The fermentation mixture is worked up as described in Example 1(c), thus producing, in addition to 0.01 g. of 3,3-ethylenedioxy-5-cholestene, 0.013 g. of 3,3-ethylenedioxy-5-androsten-17-one, m.p. 164°–165° C.

EXAMPLE 4

(a) Under the conditions disclosed in Example 1(b), 25 g. of 3β-methoxy-5-cholestene are emulsified.

(b) Under the conditions described in Example 1(c), 100 ml. of a Mycobacterium spec. NRRL-B-3805 culture is prepared. This culture is incubated for 24 hours, combined with 7 ml. of a 3-methoxy-5-cholestene suspension (corresponding to 0.25 g. of 3-methoxy-5-cholestene), and fermented for another 96 hours. The fermentation mixture is worked up as set forth in Example 1(c), thus obtaining 110 mg. of 3β-methoxy-5-androsten17-one, m.p. 141°–142° C.

EXAMPLE 5

(a) 25 g. of 4-cholesten-3-one is reacted under the conditions described in Example 2(a), but with the use of 2,2-dimethylpropanediol in place of glycol. The reaction mixture is worked up, thus obtaining 17.3 g. of 3,3-(2',2'-dimethylpropylenedioxy)-5-cholestene, m.p. 144°–145° C.

0.5 g. of 3.3-(2',2'-dimethylpropylenedioxy)-5cholestene is dissolved in 15 ml. of dimethylformamide at 60° C.

(b) 100 ml. of a Mycobacterium spec. NRRL-B-3805 culture is prepared under the conditions described in Example 1(b) and incubated for 24 hours. Then, 0.15 ml. of the 3,3-(2',2'-dimethylpropylenedioxy)-5-cholestene solution is added to the culture, and the latter is fermented for another 96 hours. The fermentation batch is worked up as described in Example 1(c), thus producing, in addition to 0.01 g. of 3,3-(2',2'-dimethylpropylenedioxy)-5-cholestene, 0.03 g. of 3,3-(2',2'-dimethylpropylenedioxy)-5-androsten-17-one, m.p. 200°–201° C.

EXAMPLE 6

(a) Under the conditions of Example 1(a), 500 ml. of a subculture of Mycobacterium spec. NRRL-B-3683 is prepared.

(b) 100 ml. of a nutrient solution according to Example 1(c) is inoculated with 10 ml. of the subculture and incubated for 24 hours. Then, the culture is combined with 1.4 ml. of a 3β-ethoxy-5-cholestene suspension prepared in accordance with Example 1(b) (corresponding to 0.05 g. of 3β-ethoxy-5-cholestene). The culture is then fermented for another 96 hours, the fermentation batch is worked up as set forth in Example 1(c), and the product, in addition to 0.005 g. of 3-ethoxy-5-cholestene, is 0.025 g. of 3β-ethoxy-5-androsten17-one, m.p. 147° C.

EXAMPLE 7

Under the conditions of Example 6, but with the use of *Mycobacterium phlei* (Institute of Health, Budapest, No. 29) or *Mycobacterium phlei* ATCC-354, 0.05 g. of 3β-ethoxy-5-cholestene yields, in addition to 0.02 g. of the starting compound, 0.015 g. of 3β-ethoxy-5-androsten-17-one.

Example 8

Under the conditions set forth in Example 6, but with the utilization of *Mycobacterium smegmatis* ATCC-20, 0.05 g. of 3β-ethoxy-5-cholestene yields 0.01 g. of 3β-ethoxy-5-androsten-17-one.

EXAMPLE 9

Under the conditions of Example 6, but with the use of *Mycobacterium smegmastis* ATCC-19979, 0.02 g. of 3β-ethoxy-5-androsten-17-one is obtained from 0.05 g. of 3β-ethoxy-5cholestene.

EXAMPLE 10

With the use of the conditions of Example 6, but with *Mycobacterium fortuitum* CBS 49, 566, 0.05 g. of 3β-ethoxy-5-cholestene yields 0.02 g. of 3β-ethoxy-5-androsten-17-one.

EXAMPLE 11

(a) Under the conditions of Example 1(a), 200 ml. of a Mycobacterium spec. NRRL-B-3805 culture is incubated at 29° C. in a 750 ml. Erlenmeyer flask.

(b) A 50-liter fermentor with 40 l. of a sterile nutrient solution containing 1.23% yeast extract (65% strength), 0.68% potassium dihydrogen phosphate, and 0.2% "Tween" 80, adjusted to pH 6.0, is inoculated with 200 ml. of the Mycobacterium spec. incubation culture, and the subculture is incubated at 29° C. for 48 hours under aeration (2 m$^3$ per hour).

(c) 200 g. of 3β-ethoxy-5-cholestene is emulsified with 80 g. of "Tegin" and 6 l. of water adjusted to pH 11.3 with sodium hydroxide solution at 95° C. for 30 minutes, using a "Dispax" reactor D-3-6-6 (company: Jahnke and Kunkel, Federal Republic of Germany). The emulsion is sterilized for 20 minutes at 120° C.

(d) A 50-liter fermentor is charged with 40 l. of a sterile nutrient solution having the same composition as described in Example 11(b) but adjusted to pH 6.5. The mixture is inoculated with 2 l. of a Mycobacterium spec. subculture and incubated for 24 hours at 29° C. under aeration (1 m$^3$ per hour) and agitation (220 r.p.m.).

Then, the 3β-ethoxy-5-cholestene emulsion prepared according to Example 11(c) is added to the culture, and the latter is fermented for another 92 hours.

After the fermentation has been accomplished, the culture is extracted three times with respectively 5 l. of ethylene chloride. The ethylene chloride extract is filtered and concentrated under vacuum.

The residue (148 g.) is chromatographed over a silica gel column, recrystallized from ethyl acetate, and the product is 83.5 g. of 3β-ethoxy-5-androsten-17-one, m.p. 145°–146.5° C.

(B) EXAMPLES OF CHEMICAL MODIFICATIONS OF THE THUS-PRODUCED 5-ANDROSTEN-17-ONE

EXAMPLE 1

(a) Under agitation, 1.5 g. of sodium borohydride is added during the course of 2 hours to a solution of 1.5 g. of 3,3-(2',2'-dimethylpropylenedioxy)-5-androsten-17-one in 75 ml. of methanol and 10 ml. of dichloromethane. The mixture is stirred for another hour, poured into ice water, extracted with dichloromethane; the dichloromethane phase is washed and concentrated under vacuum.

(b) The thus-obtained crude 3,3-(2',2'-dimethylpropylenedioxy)-5-androsten-17β-ol product is combined with 20 ml. of acetone and 4 ml. of 1N sulfuric acid and refluxed for 6 hours. The reaction mixture is allowed to cool, poured into ice water, extracted with methylene chloride, and the methylene chloride phase is washed and concentrated under vacuum. The thus-obtained crude product is recrystallized from acetone-hexane, yielding 1.0 g. of 17β-hydroxy-4-androsten-3-one, m.p. 153°–154° C.

EXAMPLE 2

Under the conditions of Example (B) 1(b), 1.5 g. of 3,3-ethylenedioxy-5-androsten-17-one is hydrolyzed and worked up, thus producing 1.1 g. of 4-androstene-3,17-dione, m.p. 172°–173.5° C.

EXAMPLE 3

Ten grams of 3β-ethoxy-5-androsten-17-one is suspended in 25 ml. of dichloromethane and 25 ml. of acetic anhydride and combined, under argon, with 0.25 ml. of boron trifluoride etherate. The reaction mixture is stirred for 2 hours at room temperature, combined with 100 ml. of water, extracted with dichloromethane, the dichloromethane phase is washed and concentrated under vacuum. The residue is chromatographed over a silica gel column, recrystallized from acetone-hexane, and the product thus obtained is 9.75 g. of 3β-acetoxy-5-androsten-17-one, m.p. 168°–170° C.

EXAMPLE 4

Five grams of 3β-methoxy-5-androsten-17-one is suspended in 5 ml. of methylene chloride and 10 ml. of enanthic anhydride. The suspension is combined with 0.2ml. of boron trifluoride ethereate and heated for 8 hours to 60° C. Then, 50 ml. of water is added to the mixture and the latter stirred for 5 hours at room temperature. After dilution with 100 ml. of methylene chloride, the mixture is extracted several times with water, the organic extract is dried with sodium sulfate, and the solvent is distilled off under vacuum. By high vacuum distillation, enanthic acid, enanthic acid ethyl ester, and a small amount of non-hydrolyzed enanthic anhydride are distilled off from the crude product at 100°–120° C. The brown residue is filtered through silica gel for purifying purposes and then recrystallized from methanol, thus obtaining 5.1 g. of 3β-enanthoyloxy-5-androsten-17-one, m.p. 68°–70° C.

EXAMPLE 5

(a) 664 mg. of lithium is reacted with 3 ml. of methyl iodide in 50 ml. of absolute diethyl ether to form a methyllithium solution. Under ice cooling, a solution of 5 g. of 3β-ethoxy-5-androsten-17-one in 50 ml. of absolute ether is added dropwise to this solution within 10 minutes, and the reaction mixture is agitated at room temperature for 5 hours.

The mixture is then combined, under ice cooling, with 30 ml. of an aqueous ammonium chloride solution, extracted with dichloromethane, and the organic phase is washed and concentrated under vacuum. The residue is recrystallized from acetone-hexane, yielding 4.6 g. of 3β-ethoxy-17α-methyl-5-androsten-17β-ol, m.p. 118°–119° C.

(b) 2.0 g. of 3β-ethoxy-17α-methyl-5-androsten-17β-ol is suspended in 5 ml. of acetic anhydride. The suspension is combined with 0.05 ml. of boron trifluoride etherate and agitated for 3 hours at room temperature.

The reaction mixture is then combined with 20 ml. of water, stirred for 2 hours, extracted with dichloromethane, and the organic phase is washed and concentrated under vacuum. The residue is purified by way of a silica gel column, and recrystallization from acetone-hexane yields 1.78 g. of 3β,17β-diacetoxy-17α-methyl-5-androstene, m.p. 142°–143° C.

(c) 0.72 g. of 3β,17β-diacetoxy-17α-methyl-5-androsten-17-one is dissolved in 15 ml. of 0.5N methanolic potassium hydroxide solution, and the solution is refluxed under argon for 6 hours.

The reaction mixture is allowed to cool, poured into 50 ml. of ice-cold sodium chloride solution, the thus-separated product is filtered off, washed, dried under vacuum, and the yield is 0.586 g. of 3β,17α-dihydroxy-17α-methyl-5-androstene as a crude product.

(d) The thus-obtained crude product is taken up in 10 ml. of benzene and 1.25 ml. of cyclohexane, combined with 0.75 g. of aluminum isopropylate, and refluxed for 2 hours. The reaction mixture is allowed to cool, acidified with dilute sulfuric acid to pH 3, diluted with water, and extracted with benzene.

The benzene extract is washed, dried, and concentrated under vacuum. The residue is recrystallized from methanol, thus obtaining 0.51 g. of 17β-hydroxy-17α-methyl-4-androsten-17-one, m.p. 162°–165° C.

EXAMPLE 6

(a) 40 g. of potassium tert.-butylate is suspended in 500 ml. of tetrahydrofuran and cooled to about 5° C. The suspension is purged with argon, and acetylene is introduced for about 90 minutes until saturation is achieved. The acetylene feed is then throttled, and within 10 minutes a solution of 50 g. of 3β-ethoxy-5-androsten-17-one in 300 ml. of tetrahydrofuran is added dropwise to the mixture. The latter is then agitated for another hour at about 5° C. The excess acetylene is removed by vacuum filtration, and the reaction mixture is combined with 250 ml. of methanol. Under intense ice cooling, 47.5 ml. of concentrated hydrochloric acid is then added dropwise to the reaction mixture within 10 minutes.

The organic solvent is then distilled off under vacuum, replaced by water, the suspension cooled for 2 hours to 0° C., the precipitate filtered off, washed, and dried for 16 hours under vacuum at 50° C., thus obtaining 52.4 g. of 17α-ethynyl-3-ethoxy-5-androsten-17β-ol as a crude product which melts, after recrystallization from acetone-hexane, at 201°–204° C.

(b) 3.0 g. of the thus-obtained 17α-ethynyl-3-ethoxy-5-androsten-17β-ol is combined with 30 ml. of acetic anhydride and 0.1 ml. of boron trifluoride etherate and agitated for 60 minutes at room temperature. The reaction mixture is worked up as described in Example (B)5(c), thus obtaining, after recrystallization from ethyl acetate, 2.95 g. of 3β,17β-diacetoxy-17α-ethynyl-5-androstene, m.p. 160°–162° C.

(c) Under the conditions described in Example (B)5(d), 1.38 g. of 3β,17β-diacetoxy-17α-ethynyl-5-androstene is reacted with 30 ml. of 0.5N methanolic potassium hydroxide solution and then worked up, thus producing 1.2 g. of 17α-ethynyl-3β,17β-dihydroxy-5-androstene as a crude product.

(d) 1.19 g. of the thus-obtained 17α-ethynyl-3β,17β-dihydroxy-5-androstene crude product is oxidized in 20 ml. of acetone at −10° C. with 8N chromic acid solution in accordance with the Jones method. The reaction mixture is extracted with dichloromethane, the dichloromethane phase is washed, concentrated under vacuum, the residue taken up in 10 ml. of dioxane and 1 ml. of 1N hydrochloric acid, and the mixture is heated under reflux for 30 minutes.

The reaction mixture is then neutralized with sodium bicarbonate solution, extracted with dichloromethane, the dichloromethane phase is washed and concentrated under vacuum.

The residue is chromatographed over a silica gel column, recrystallized from acetone-hexane, and the yield is 0.99 g. of 17α-ethynyl-17β-hydroxy-4-androsten-3-one, m.p. 264°–266° C.

EXAMPLE 7

(a) 52.38 g. of 17α-ethynyl-3β-ethoxy-5-androsten-17α-ol crude product [prepared according to Example (B)6(a)] is dissolved in 400 ml. of toluene and 79.3 ml. of 2,4-lutidine, then combined with a solution of 35 ml. of distilled phosphorus oxychloride in 125 ml. of toluene, and thereafter heated for 7 hours to a reaction temperature of 100° C.

The reaction mixture is allowed to cool, acidified with 1N sulfuric acid to pH 1, diluted with ether, the organic phase washed and dried with sodium sulfate, and concentrated under vacuum. The residue is recrystallized from methanol after chromatography over a silica gel column, thus obtaining 32.13 g. of 17-ethynyl-3β-ethoxy-5,16-androstadiene, m.p. 155° to 160° C.

(b) 28.53 g. of 17-ethynyl-3β-ethoxy-5,16-androstadiene is dissolved in 1,400 ml. of methanol and 300 ml. of tetrahydrofuran and heated to 60° C. A suspension of 3.19 g. of mercury (II) oxide in 61 ml. of water and 2.66 ml. of concentrated sulfuric acid, heated prior to addition for 30 minutes to 60° C., is then added to the solution, and the mixture is heated for 10 minutes under reflux.

The reaction mixture is thereafter concentrated exhaustively under vacuum, the residue taken up in 1,000 ml. of dichloromethane, the organic phase is washed, concentrated under vacuum, and the yield is 30.7 g. of 3β-ethoxy-5,16-pregnadien-20-one as the crude product which melts at 144°–146° C. after recrystallization from diisopropyl ether.

(c) 5.5 g. of 3β-ethoxy-5,16-pregnadien-20-one crude product is combined with 60 ml. of methanol, 1 ml. of 1N sodium hydroxide solution, and 1 g. of Raney nickel and hydrogenated for 2 hours at room temperature. The catalyst is then filtered off, washed with methanol, the methanol solutions are concentrated and the yield is 5.3 g. of 3β-ethoxy-5-pregnen-20-one as the crude product.

(d) 5.3 g. of the thus-prepared 3β-ethoxy-5-pregnen-20-one crude product is combined with 15 ml. of acetic anhydride, 15 ml. of dichloromethane, and 0.15 ml. of boron trifluoride etherate and agitated for 2 hours at room temperature.

The reaction mixture is then combined with water and dichloromethane, the organic phase is separated, washed, and concentrated under vacuum.

(e) The thus-obtained 3β-acetoxy-5-pregnen-20-one crude product is dissolved in 100 ml. of methanol, combined with 10 ml. of 1N aqueous sodium hydroxide solution, and refluxed under nitrogen for 2 hours.

The reaction mixture is then allowed to cool, poured into 250 ml. of ice water, the thus-separated product is vacuum-filtered, washed, and dried under vacuum at 60° C. The crude product obtained thereby is recrystallized from methanol, yielding 4.53 g. of 3β-hydroxy-5-pregnen-20-one, m.p. 191°–193° C.

(f) 10.25 g. of 3β-hydroxy-5-pregnen-20-one is combined with 200 ml. of benzene, 25 ml. of cyclohexanone, and 15 g. of aluminum isopropylate and refluxed for 2 hours.

The reaction mixture is then allowed to cool, acidified with 1N sulfuric acid to pH 3, combined with 200 ml. of benzene, the organic phase is washed, dried, and concentrated under vacuum. The residue is recrystallized from diisopropyl ether, thus obtaining 8.93 g. of 4-pregnene-3,20-dione, m.p. 127°–129° C.

EXAMPLE 8

(a) A Grignard solution, prepared from 8.72 g. of magnesium filings, 22.53 ml. of methylene iodide, and 250 ml. of absolute ether, is combined with 500 ml. of absolute tetrahydrofuran. The ether is distilled off until an internal temperature of 60° C. has been reached. The solution is then cooled to about 0° C., combined with 1.55 g. of copper (I) chloride, agitated for 20 minutes, mixed within 30 minutes with a solution of 30.7 g. of 3β-ethoxy-5,6-pregnadien-20-one crude product [prepared according to Example (B)7(b)] in 250 ml. of absolute tetrahydrofuran, and the mixture is stirred for another hour at 0° C.

Thereafter, 360 ml. of 1N sulfuric acid is added dropwise to the reaction mixture, the latter is combined with 1,000 ml. of ether, washed with semisaturated sodium chloride solution, and the organic phase is concentrated under vacuum. The residue is chromatographed over a silica gel column, and recrystallization from diisopropyl ether yields 28.8 g. of 3β-ethoxy-16α-methyl-5-pregnen-20-one, m.p. 84°–86° C.

(b) A solution of 10 g. of 3β-ethoxy-16α-methyl-5-pregnen-20-one in 25 ml. of acetic anhydride and 25 ml. of dichloromethane is combined, under argon, with 0.25 ml. of boron trifluoride etherate and agitated for 6 hours at room temperature.

The reaction mixture is then combined with 100 ml. of water, agitated for 2 hours at room temperature, diluted with dichloromethane, the organic phase is washed and concentrated under vacuum. The residue is chromatographed over a silica gel column. Recrystallization from diisopropyl ether yields 8.9 g. of 3β-acetoxy-16α-methyl-5-pregnen-20-one, m.p. 181°–184° C.

The further reaction of this compound to obtain pharmacologically active steroids, such as, for example 6α-fluoro-11β,21-dihydroxy-16-methyl-1,4-pregnadien-3,20-dione, is conventional (J. Chem. Soc., London [1959]:3595; and German Pat. No. 1,169,444).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the production of 17-keto steroids of the androstane series by subjecting a steroid having a sterol hydrocarbon side chain at the 17-position to the oxidative degradation activity of a culture of microorganism which degrades sterol side chains to 17-keto group, the improvement which comprises conducting the fermentation in the absence of an inhibitor which inhibits attack on the ring system and employing as the starting steroid a sterol derivative of the formula

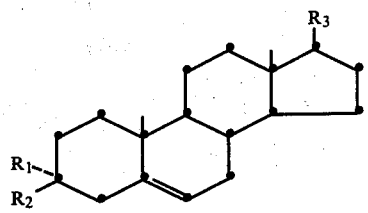

wherein $R_1$ is a hydrogen atom and $R_2$ is alkoxy of 1–4 carbon atoms or $R_1$ and $R_2$ collectively are alkylenedioxy of 2–6 carbon atoms and 2–3 carbon atoms bridging the oxygen atom and $R_3$ is a sterol hydrocarbon side chain of 8–10 carbon atoms.

2. A process according to claim 1, wherein the microorganism is a species of the genera Arthrobacter, Brevibacterium, Microbacterium, Protaminobacter, Bacillus, norcardia, Streptomyces, or Mycobacterium.

3. A process according to claim 1, wherein the microorganism is a species of the genera Mycobacterium.

4. A process according to claim 1, wherein the microorganism is a species of the genera Mycobacterium spec. NRRL-B-3805.

5. A process according to claim 1, wherein $R_1$ and $R_2$ collectively are alkylenedioxy.

6. A process according to claim 1, wherein the sterol derivative is a compound of the formula

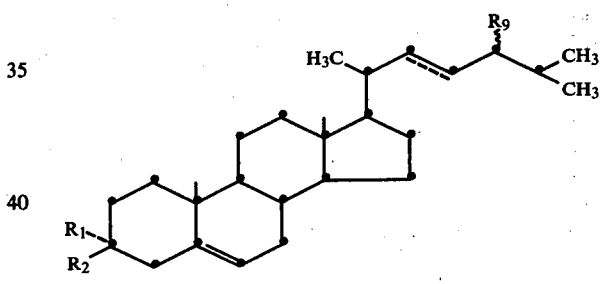

wherein $R_1$ and $R_2$ have the values given therein, the bond ==== is a single or double bond, and $R_9$ is hydrogen atom, methyl or ethyl.

7. A process of claim 1 wherein $R_1$ is a hydrogen atom and $R_2$ is alkoxy of 1–4 carbon atoms.

8. A process of claim 7 wherein the microorganism is a species of the general Mycobacterium.

9. A process of claim 7 wherein the microorganism is a species of the genera Mycobacterium spec. NRRL-B-3805.

10. A process of claim 5 wherein the microorganism is a species of the genera Mycobacterium spec. NRRL-B-3805.

* * * * *